United States Patent [19]

Morris

[11] Patent Number: 4,596,245
[45] Date of Patent: Jun. 24, 1986

[54] ENDOUROLOGICAL DRAPE

[75] Inventor: Henrietta K. Morris, Arlington, Tex.

[73] Assignee: Surgikos, Inc., Arlington, Tex.

[21] Appl. No.: 690,786

[22] Filed: Jan. 11, 1985

[51] Int. Cl.[4] .............................................. A61B 19/06
[52] U.S. Cl. ................................................ 128/132 D
[58] Field of Search ............... 128/132 D, 132 R, 155, 128/156; 604/322

[56] References Cited

U.S. PATENT DOCUMENTS

| | | | |
|---|---|---|---|
| 4,134,398 | 1/1979 | Scrivens | 128/132 D |
| 4,192,312 | 3/1980 | Wilson | 128/132 D |
| 4,196,723 | 4/1980 | Moose, Jr. | 128/132 D |
| 4,316,455 | 2/1982 | Stoneback | 128/132 D |
| 4,323,062 | 4/1982 | Canty | 128/132 D |
| 4,378,794 | 5/1983 | Collins | 128/132 D |
| 4,462,396 | 7/1984 | Wichman | 128/132 D |
| 4,476,860 | 10/1984 | Collins et al. | 128/132 D |

Primary Examiner—John J. Wilson
Assistant Examiner—James Hakomaki
Attorney, Agent, or Firm—Michael Q. Tatlow

[57] ABSTRACT

A surgical drape for endourological procedures is disclosed. The drape has a plurality of tube holders on the surface of the drape, a fluid collection bag with strips to hold the bag open during the procedure, and a fenestration specifically adapted for endourological procedures.

2 Claims, 2 Drawing Figures

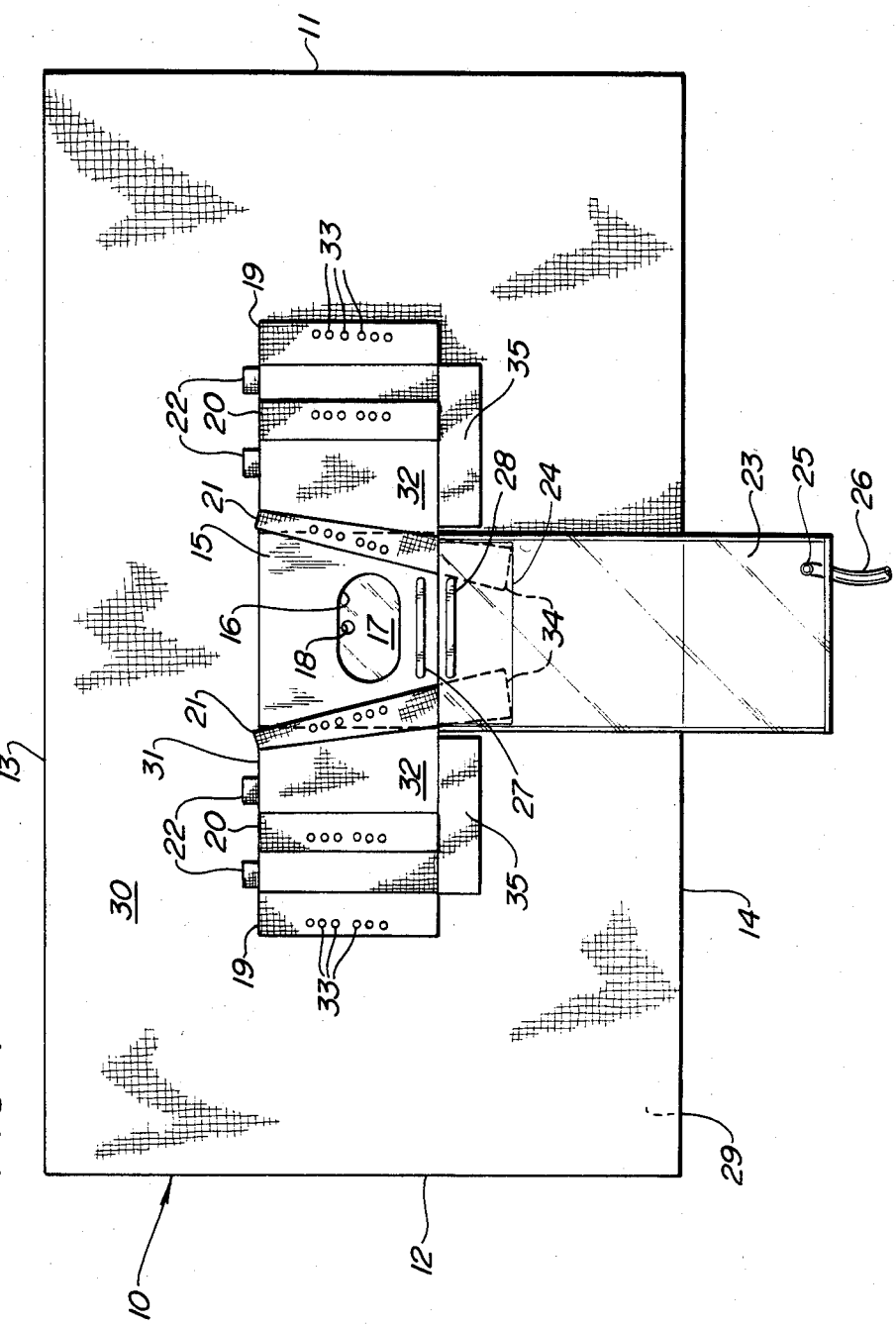

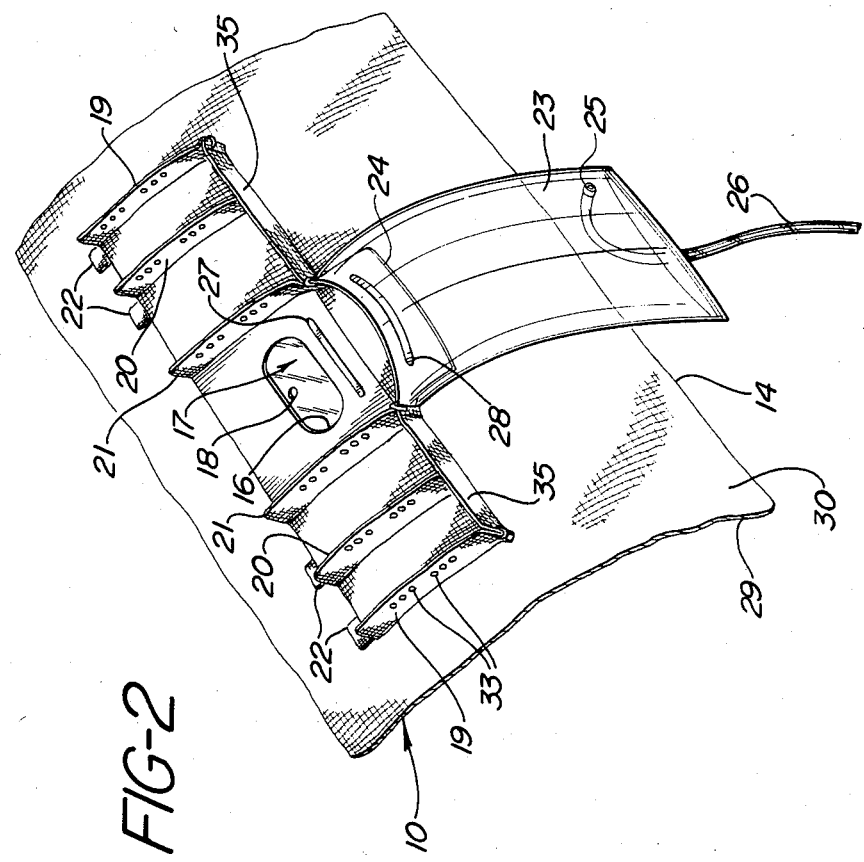

ENDOUROLOGICAL DRAPE

FIELD OF THE INVENTION

The present invention relates to surgical drapes and more particularly to a surgical drape specifically adapted to be used in certain endourological procedures, specifically nephroscopy, nephrolithotomy and nephrolithotripsy procedures.

PRIOR ART

Surgical drapes are customarily used in the operating room to protect the site of the operation from possible contamination from bacteria which may be found on other portions of the patient's body or which may be airborne or conveyed to the operative site by operating room personnel. The use of surgical drapes is generally considered to be necessary to isolate the patient from the operating room environment and from the operating room staff. The drapes are usually placed over the patient to completely isolate the patient other than that portion of the patient's body which is the actual site of the surgical procedure.

Surgical drapes which provide some mechanism for the direction of body fluids or operating room fluids have previously been known. For example, U.S. Pat. No. 3,791,382 discloses a surgical drape construction which provides a pocket in the outer surface of the drape to receive fluid runoff from the site of the surgical procedure. U.S. Pat. Nos. 4,076,017 and 4,105,019 disclose surgical drapes in which the pocket is formed on the outer surface of the drape by folding an edge of the drape upon itself and sealing it together. U.S. Pat. No. 4,169,472 discloses a surgical drape which includes an impervious bag used for collecting liquids and other fluids which may be present during the operating procedure. U.S. Pat. Nos. 4,378,794; 4,414,968 and 4,462,396 disclose surgical drapes for cystoscopy procedures and these drapes which include some type of fluid collection bag.

Surgical drapes which include an incise film are also known. An incise film is a clear plastic film with adhesive on the patient contact side of the film. The film is adhered to the patient over the operative site. The surgical incision is made through the film and the patient's skin. Incise films are considered to be advantageous to prevent bacterial migration from the patient's skin which is adjacent the surgical incision site. Examples of such drapes are disclosed in U.S. Pat. Nos. 3,826,253; 4,027,665 and 4,489,720.

Tubing or cord holders of various types have also been used on surgical drapes. Examples of tube or cord holders are disclosed in U.S Pat. Nos. 3,721,234; 3,881,474 and 4,323,062.

Although all of the above-mentioned drapes disclose constructions that can be used to collect fluids and hold tubing, the construction of the drapes is not entirely suitable for endourological procedures generally, and such drapes are not suitable for the newly developed percutaneous nephrolithotripsy procedure. The percutaneous nephrolithotripsy procedure is a method of breaking kidney stones using ultrasonic vibrations. In the procedure, a percutaneous incision is made in the patient, and an angiographic guide wire is inserted into the kidney, aided by fluoroscopy, to the vicinity of the stone. The stone itself can be broken with a nephroscope which has an ultrasonic lithotriptor at the end of the scope. When the ultrasonic lithotriptor is in the vicinity of the stone, ultrasonic vibrations will break up the stone, which can be flushed from the kidney with irrigation fluids. This procedure utilizes very large amounts of irrigation fluids and employs a large number of sophisticated medical instruments including angiographic guide wires, an endoscope, pigtail catheter, dialators, a nephroscopy tube containing the ultrasonic lithotriptor, as well as tubing to direct fluid into the operative site and suction tube to remove excess fluid. Prior to the present invention, there was no surgical drape specifically adapted to be used in the nephrolithotripsy procedure. Because of the large amounts of fluid used and the multiplicity of sophisticated surgical instrumentation that is used in these procedures, drapes which have been developed for other procedures were not suitable for use in the nephrolithotripsy procedure.

SUMMARY OF THE INVENTION

The present surgical drape provides multiple tubing guides to hold liquid and suction tubing in place, as well as to provide for the placement of various wires and ready placement of instruments that are used in nephroscopy procedures. The drape employs a fluid collection bag with a large capacity and has a fenestration which is particularly useful in nephrolithotripsy procedures.

Other features of the present invention will be readily apparent to one skilled in the art from the description of the invention which follows.

BRIEF DESCRIPTION OF THE DRAWINGS

FIG. 1 is a top plan view of the surgical drape of the present invention.

FIG. 2 is a fragmentary, isometric view of the central region of the drape of the present invention.

DETAILED DESCRIPTION OF THE INVENTION

The surgical drape of the present invention is generally shown in FIG. 1. The drape has a main sheet 10, which has a top edge 11, a bottom edge 12 and two opposing side edges 13 and 14. The drape has a lower surface 29 which is in contact with the body of the patient and an upper surface 30 which is opposite the lower surface. The drape has a reinforcement area 31 generally located in the central region on the upper surface of the main sheet. The center of the reinforcement area consists of a plastic film 15. There is a fenestration 16 through the plastic film and the main sheet. There is a transparent plastic film 17 which overlies the fenestration. The plastic film 17 has an adhesive coating on its lower surface which will be in contact with the skin of the patient and which aids in securing the drape to the surface of the skin of the patient. There is a small circular fenestration 18 in the incise film. The portion of the reinforcement, other than the plastic film, and which is shown in the drawing as 32, may be an absorbent nonwoven fabric backed with a plastic film which is secured directly to the upper surface of the main sheet. There are a series of tube holders 19, 20 and 21 attached to the reinforcement area of the drape. The tube holders may be formed by doubling over the reinforcing fabric. One edge of the tube holders is secured to the upper surface of the main sheet, and the other edge is not attached, so that the tube holders may be turned perpendicular to the upper surface of the main sheet. The tube holders have a multiplicity of holes 33 through them to accommodate threading wires and tubings through the holes to keep them in the vicinity of the operative site, which would be the area of the fenestration. The holes 33 in the tube holders are aligned with the holes in the other tube holders. There can be any number of holes in the tube holders, but there should be at least three in each of the tube holders to accommodate the various wires and tubing used in the procedure. The tube holders 21, which are adjacent the fenestration, have extended ends 34 which extend into a plastic fluid collection bag 23 to direct fluid into the bag. The fluid collection bag has a piece of nonwoven fabric or a screen 24 to trap stone particles or dropped instruments. There is a port 25 at the bottom of the bag which may be connected to tubing 26 to empty the bag if necessary. There may also be clamping tabs 22 around the edges of the reinforcement area to provide additional sites to clamp various surgical instruments to the upper surface of the drape. There are flaps 35 at the lower edges of the reinforcement area adjacent the fluid collection bag. These flaps can be bent upward from the upper surface of the main sheet and can be clamped to the tube holders to form instrument bags into which instruments can be placed during the surgical procedure. This is shown in FIG. 2. The edges of the flaps 35 are clamped with surgical clamps to the edges of the tube holders to form a surface into which instruments can be readily placed.

There is a moldable strip 27, made from metal or a moldable plastic, secured on the upper surface of the plastic portion of the reinforcement area between the fenestration and the fluid collection bag. There is a second moldable strip 28 secured to the upper portion of the plastic bag. This is shown in both FIGS. 1 and 2. The strips can be bent and are capable of being maintained in a fixed configuration after bending. This allows the strip 27 to be bent to conform to the body of the patient and the strip 28 to be bent in a concave fashion to allow the fluid collection bag to be maintained in an open condition and assist in directing fluid into the bag.

The small circular fenestration 18 in the incise sheet is used in the procedure to allow the angiographic wires to be fed from the body of a patient and through the fenestration 18 when the drape is placed on a patient. The angiographic guide wires are very often placed in the patient prior to the patient being sent to the operating room. These wires would be placed by the radiology department, as it is necessary that the placement be done with a fluoroscope or other imaging equipment.

The drape may be folded into a compact form to allow the drape to be readily placed on the body of the patient. The incise film 27, which has adhesive on the patient side, is usually covered with a release sheet which is removed from the adhesive prior to the placement of the drape on the patient. When the drape is placed on the patient, the release sheet is removed, the angiographic guide wires would be fed through the fenestration hole 18 and the incise sheet 17, and then the drape would be placed on the patient. After the drape is in place on the patient, the various wires and tubes for the instruments used in the procedure may be threaded through the holes 33 in the tubing holders 19, 20 and 21 to locate the wires and tubes in the vicinity of the fenestration 16 in the drape.

What is claimed:

1. A surgical drape comprising a rectangular main sheet having a top edge, bottom edge and two opposing side edges, and an upper surface and a lower surface, a reinforcement area over the upper surface of the drape in a central location, a plastic film in the center of the reinforcement area, a fenestration through the plastic film and through the main sheet, a transparent film overlying the fenestration with an adhesive coating on the lower surface of the film, a circular fenestration through the transparent film, a fluid collection bag secured to the upper surface of the drape at a location between the fenestration and a side edge of the drape, a moldable strip located on the upper surface of the reinforcement area at a location between the fenestration and the fluid collection bag and bendable to conform to the body of a patient, a second moldable strip located on the top portion of the fluid collection bag and bendable to a concave configuration, the bent moldable strips maintaining the fluid collection bag in an open condition, a multiplicity of tubing holders located along the reinforcement area and capable of being formed into flaps extending perpendicular to the surface of the main sheet and a plurality of openings in each of the tubing holders capable of receiving tubing and wires.

2. The surgical drape of claim 1 in which the tubing holders adjacent the fenestration extend into the fluid collection bag to direct fluid into the bag.

* * * * *